United States Patent [19]

Arney

[11] Patent Number: 5,232,446
[45] Date of Patent: Aug. 3, 1993

[54] MULTI-SINUS PERFUSION BALLOON DILATATION CATHETER

[75] Inventor: Michelle Arney, Minneapolis, Minn.

[73] Assignee: SciMed Life Systems, Inc., Maple Grove, Minn.

[21] Appl. No.: 784,968

[22] Filed: Oct. 30, 1991

[51] Int. Cl.⁵ .................................. A61M 29/00
[52] U.S. Cl. ........................... 604/96; 604/101; 606/194
[58] Field of Search ............... 604/96, 101–103; 606/192, 194

[56] References Cited

U.S. PATENT DOCUMENTS

| | | | |
|---|---|---|---|
| B1 4,762,129 | 7/1991 | Bonzel | 606/194 |
| 3,774,596 | 11/1973 | Cook | 606/192 |
| 4,183,102 | 1/1980 | Guiset | 3/1.4 |
| 4,342,316 | 8/1982 | Rosenberg | 604/103 |
| 4,423,725 | 1/1984 | Baran et al. | 128/207.15 |
| 4,484,579 | 11/1984 | Meno et al. | 606/194 |
| 4,581,017 | 4/1986 | Sahota | 604/101 |
| 4,585,000 | 4/1986 | Hershenson | 128/345 |
| 4,661,094 | 4/1987 | Simpson | 604/53 |
| 4,762,129 | 8/1988 | Bonzel | 128/344 |
| 4,771,777 | 9/1988 | Horzewski et al. | 128/344 |
| 4,787,388 | 11/1988 | Hofmann | 128/344 |
| 4,790,315 | 12/1988 | Mueller, Jr. et al. | 128/344 |
| 4,820,271 | 4/1989 | Deutsch | 604/99 |
| 4,850,969 | 7/1989 | Jackson | 604/96 |
| 4,877,031 | 10/1989 | Conway et al. | 128/344 |
| 4,878,495 | 11/1989 | Grayzel | 604/101 |
| 4,892,519 | 2/1990 | Songer et al. | 604/96 |
| 4,901,731 | 2/1990 | Millar | 128/675 |
| 4,909,252 | 3/1990 | Goldberger | 606/194 |
| 4,932,413 | 6/1990 | Shockey et al. | 128/657 |
| 4,944,745 | 7/1990 | Sogard et al. | 606/194 |
| 4,983,167 | 2/1991 | Sahota | 606/194 |
| 5,000,734 | 3/1991 | Boussignac et al. | 604/96 |
| 5,000,743 | 3/1991 | Patel | 606/194 |
| 5,002,531 | 3/1991 | Bonzel | 604/96 |
| 5,078,685 | 1/1992 | Colliver | 604/96 |
| 5,108,370 | 4/1992 | Walinsky | 604/96 |

Primary Examiner—John D. Yasko
Assistant Examiner—Anthony Gutowski
Attorney, Agent, or Firm—Kinney & Lange

[57] ABSTRACT

A perfusion dilatation balloon catheter is formed by a balloon having opposing intermediate chamber surfaces connected by a seal along the length of the balloon to form two symmetrical, communicating segments of the balloon. The outer surface of the balloon, which is common to both segments, incurves as the balloon is inflated causing the segments to juxtapose. The outer surfaces of the two segments cooperate to dilate the wall of an artery. The outer surfaces of the segments further define two sinuses adjacent to the juxtaposed outer surfaces of the segments, which allow passive perfusion of blood through the balloon during a dilatation procedure.

17 Claims, 6 Drawing Sheets

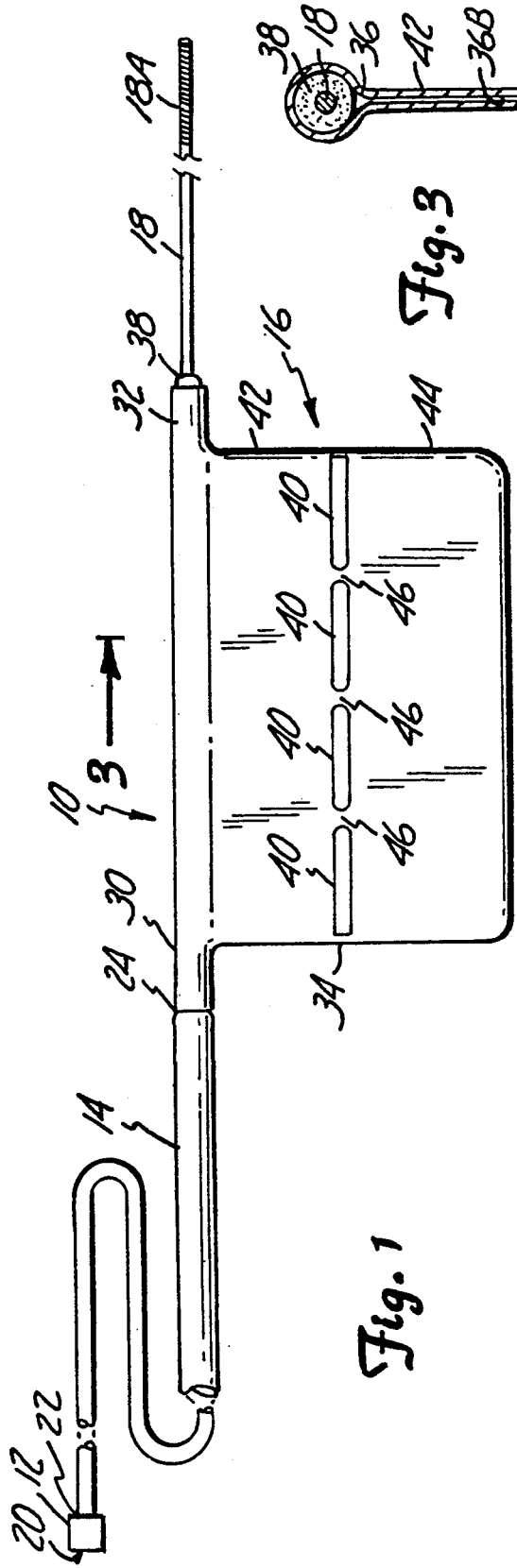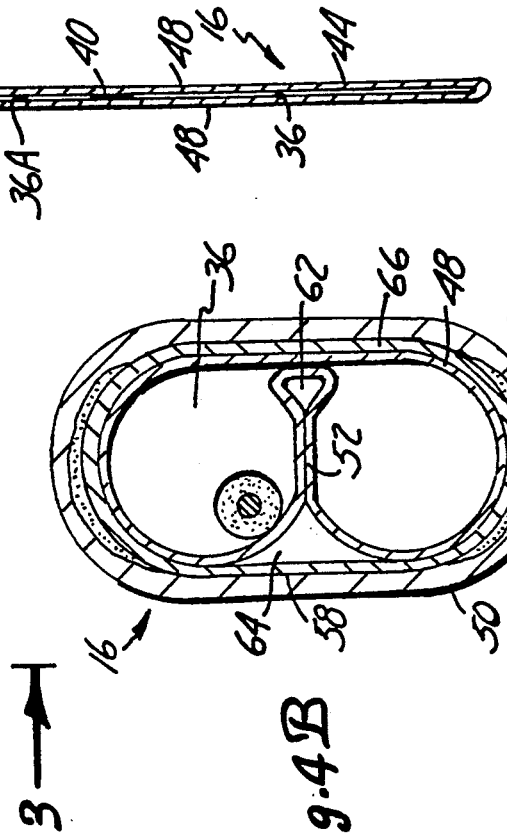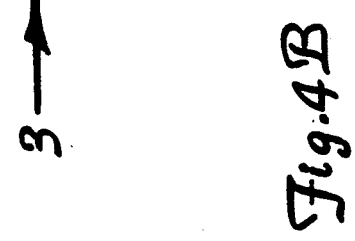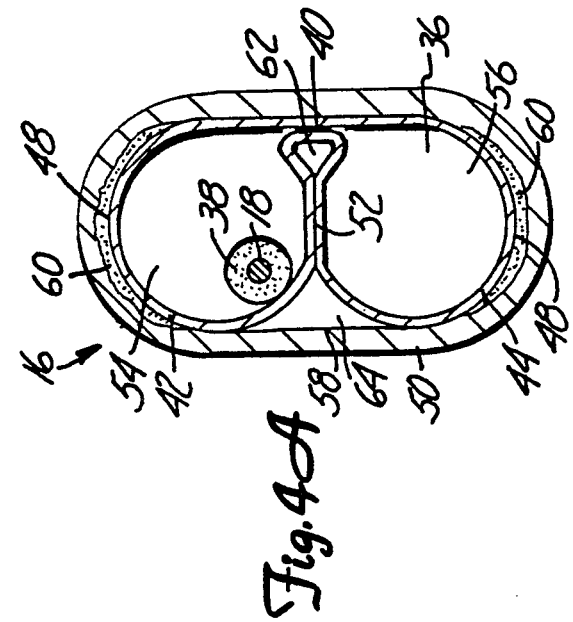

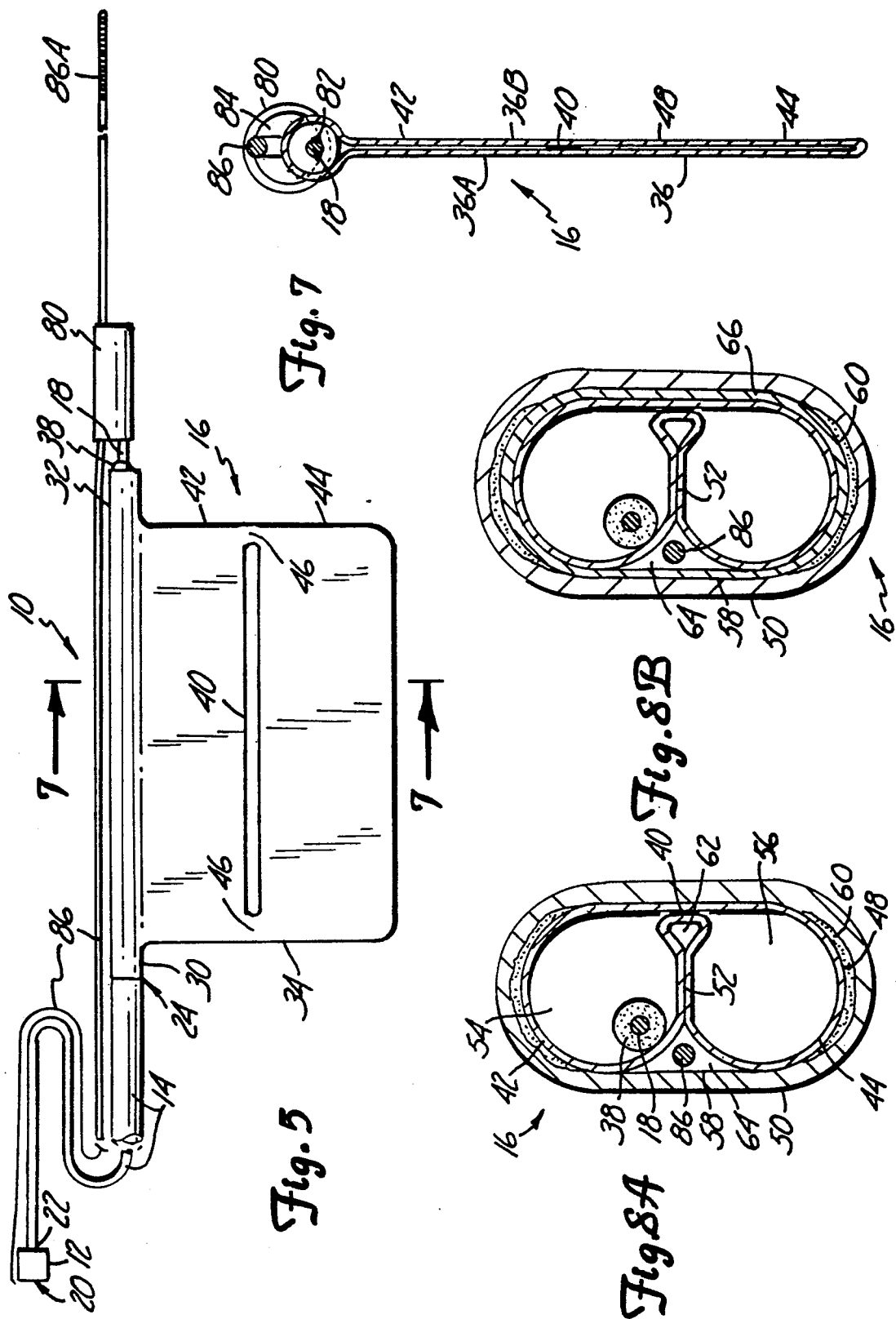

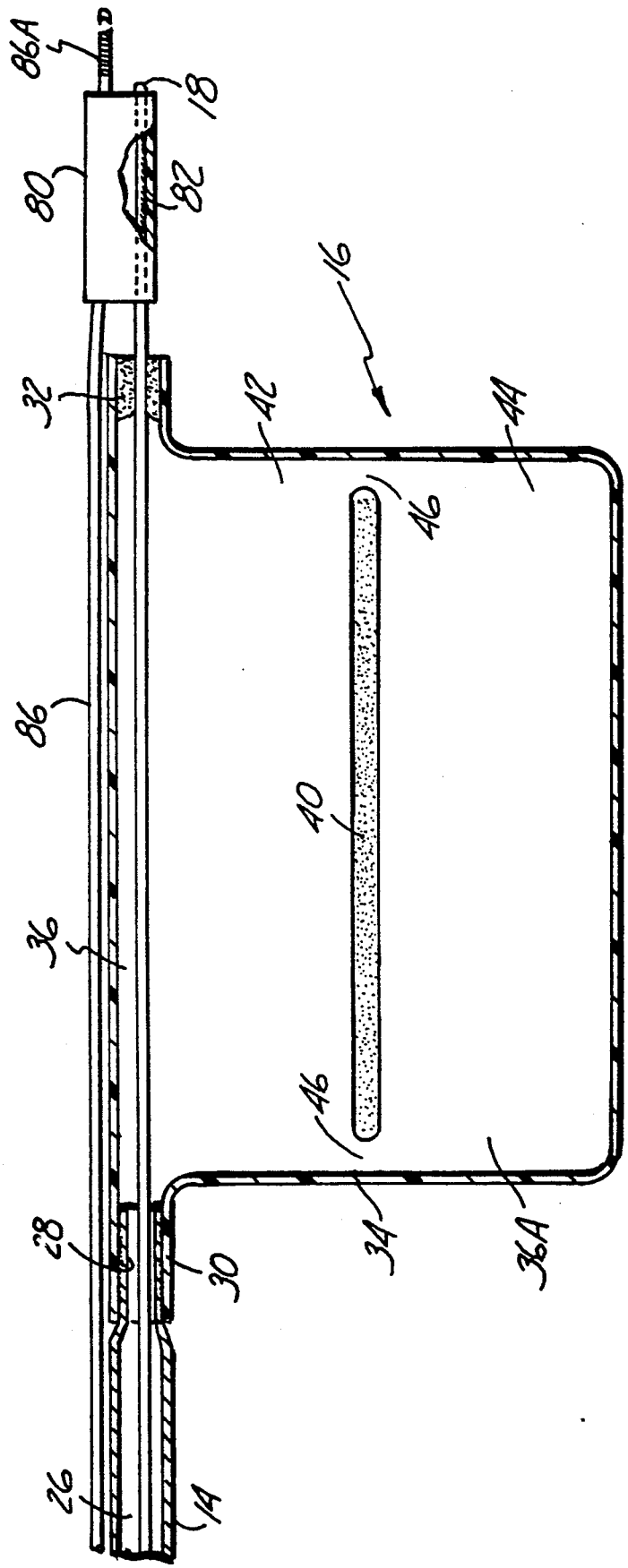

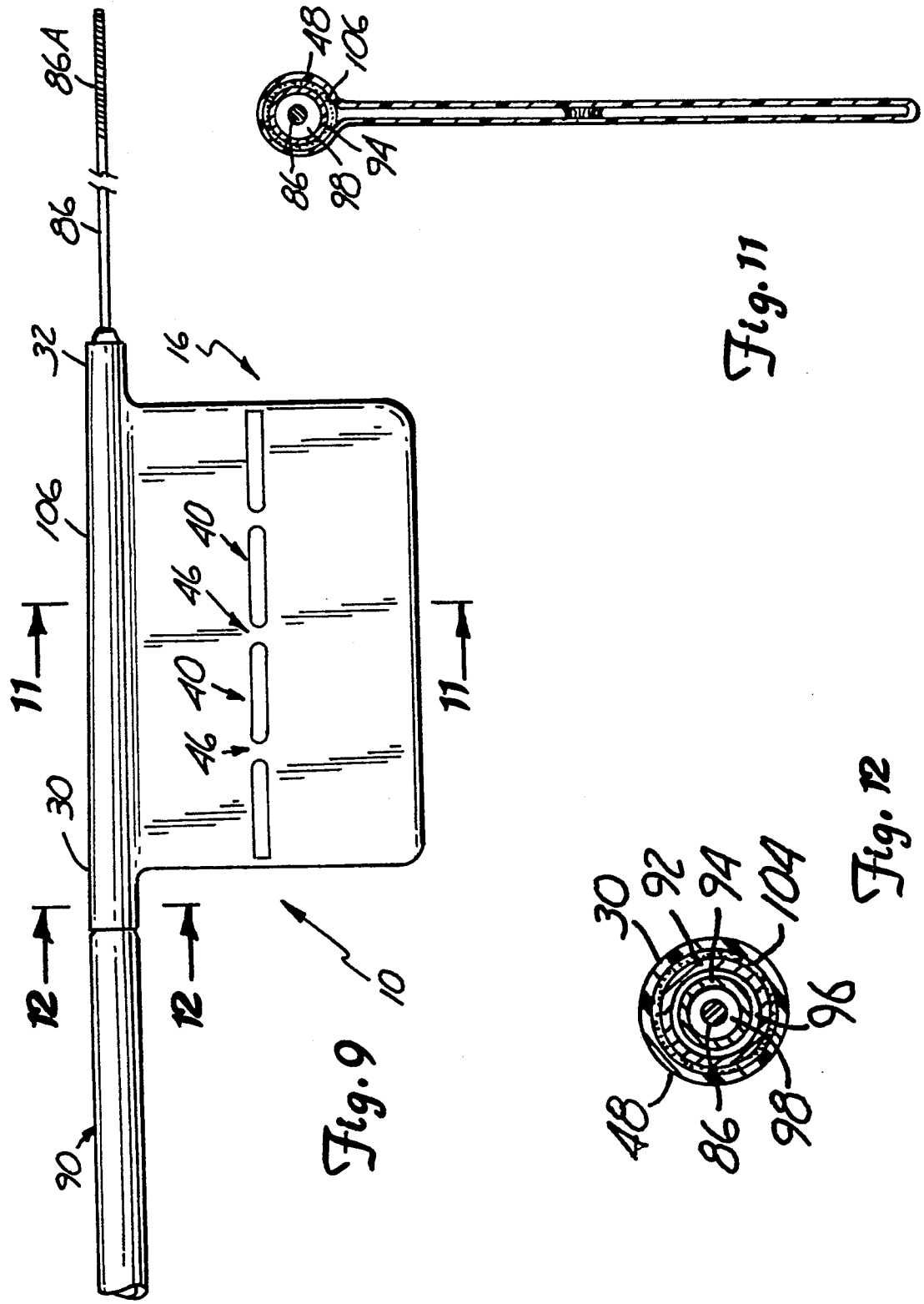

MULTI-SINUS PERFUSION BALLOON DILATATION CATHETER

BACKGROUND OF THE INVENTION

The present invention relates to the field of angioplasty. In particular, the present invention relates to a balloon catheter which provides prolonged dilatations of coronary arteries without blocking blood flow by utilizing passive perfusion.

Angioplasty has gained wide acceptance as an efficient, effective and alternative method of removing undesirous restrictions caused by tissue growth or lesions on the inner walls of the blood vessels. Such tissue growth or lesions cause a narrowing of the blood vessels called a "stenosis" which severely restricts or limits the flow of blood. In the most widely used form of angioplasty, a dilatation catheter, which has an inflatable balloon at its distal end, is guided through the vascular system. With the aid of fluoroscopy, a physician is able to position the balloon across the stenosis. The balloon is then inflated by applying fluid pressure through an inflation lumen of the catheter to the balloon. Inflation of the balloon stretches the artery and presses the stenosis-causing lesion into the artery wall to remove the constriction and re-establish acceptable blood flow through the artery.

One disadvantage of many dilatation catheters of the prior art is the complete occlusion of the blood vessel that results while the balloon is inflated. Prolonged complete blockage of a coronary artery poses serious risk of damage to the tissue downstream from the occlusion which is deprived of oxygenated blood. This consequence poses a severe limitation on the length of time the balloon can remain expanded within an artery to effectively remove the stenosis. Longer inflation times increase the probability that the artery will remain open after the catheter is removed.

Various methods for providing passive perfusion of blood through or past the inflated balloon are found in the following prior art references: Baran et al. U.S. Pat. No. 4,423,725; Sahota U.S. Pat. No. 4,581,017; Hershenson U.S. Pat. No. 4,585,000; Horzewski et al. U.S. Pat. No. 4,771,777; Mueller et al. U.S. Pat. No. 4,790,315; Songer et al. U.S. Pat. No. 4,892,519; Goldberger U.S. Pat. No. 4,909,252; Sogard et al. U.S. Pat. No. 4,944,745; Sahota U.S. Pat. No. 4,983,167 and European Patent Application 0 246 998; Boussignac et al. U.S. Pat. No. 5,000,734; Patel U.S. Pat. No. 5,000,743; and Bonzel U.S. Pat. No. 5,002,531.

There is still a need in the field, however, for a perfusion dilatation catheter with an optimal perfusion cavity which permits good arterial blood flow during a dilatation procedure, and is capable of being manufactured with relative ease and minimal cost.

SUMMARY OF THE INVENTION

The present invention is a multi-sinus perfusion balloon dilatation catheter which includes a shaft with a lumen and an inflatable multi-segment balloon disposed at the distal end of the shaft. The multi-segment balloon is formed from an inflatable single-chambered balloon with an intermediate seal which bisects a width of the balloon to form two generally symmetrical segments of the balloon. The seal connects opposing intermediate surfaces of the balloon chamber along the length of the balloon, with spaced interruptions of the seal permitting fluid passage from one segment to the other for inflation and deflation of the balloon segments. One segment of the balloon is connected to a distal end of the shaft and is in fluid communication with the shaft lumen.

Under fluid pressure, the two segments of the balloon inflate and incurve; the outer surfaces of each segment juxtapose to form a generally cooperative outer surface, which interacts with an artery wall, and sinuses adjacent to the juxtaposed outer segment surfaces, which permits passive perfusion of blood past the inflated balloon. The multi-segment balloon of the present invention, therefore, is capable of remaining inflated within an artery for prolonged lengths of time and therefore reduces the risk of damage to the tissue downstream from the inflated balloon.

BRIEF DESCRIPTION OF THE DRAWINGS

FIG. 1 is a top view of a preferred embodiment of the perfusion balloon dilatation catheter of the present invention.

FIG. 3 is a cross-sectional view of the balloon taken along line 3—3 of FIG. 1.

FIG. 4A is a cross-sectional view of the balloon of FIG. 3 shown inflated within an artery.

FIG. 4B is a cross-sectional view of the balloon of FIG. 3 shown with a sheath around an inflated balloon within an artery.

FIG. 5 is a top view of a second embodiment of the perfusion balloon dilatation catheter of the present invention.

FIG. 6 is a longitudinal sectional view of the balloon of FIG. 5.

FIG. 7 is a cross-sectional view of the balloon taken along line 7—7 of FIG. 5.

FIG. 8A is a cross-sectional view of the balloon of FIG. 7 showing the balloon inflated within an artery.

FIG. 8B is a cross-sectional view of the balloon of FIG. 7 showing a sheath around an inflated balloon within an artery.

FIG. 9 is a top view of a third embodiment of the perfusion balloon dilatation catheter of the present invention.

FIG. 11 is a cross-sectional view of the balloon taken along line 11—11 of FIG. 9.

FIG. 12 is a cross-sectional view of the balloon taken along line 12—12 of FIG. 9.

DETAILED DESCRIPTION OF THE PREFERRED EMBODIMENTS

Figure 2:
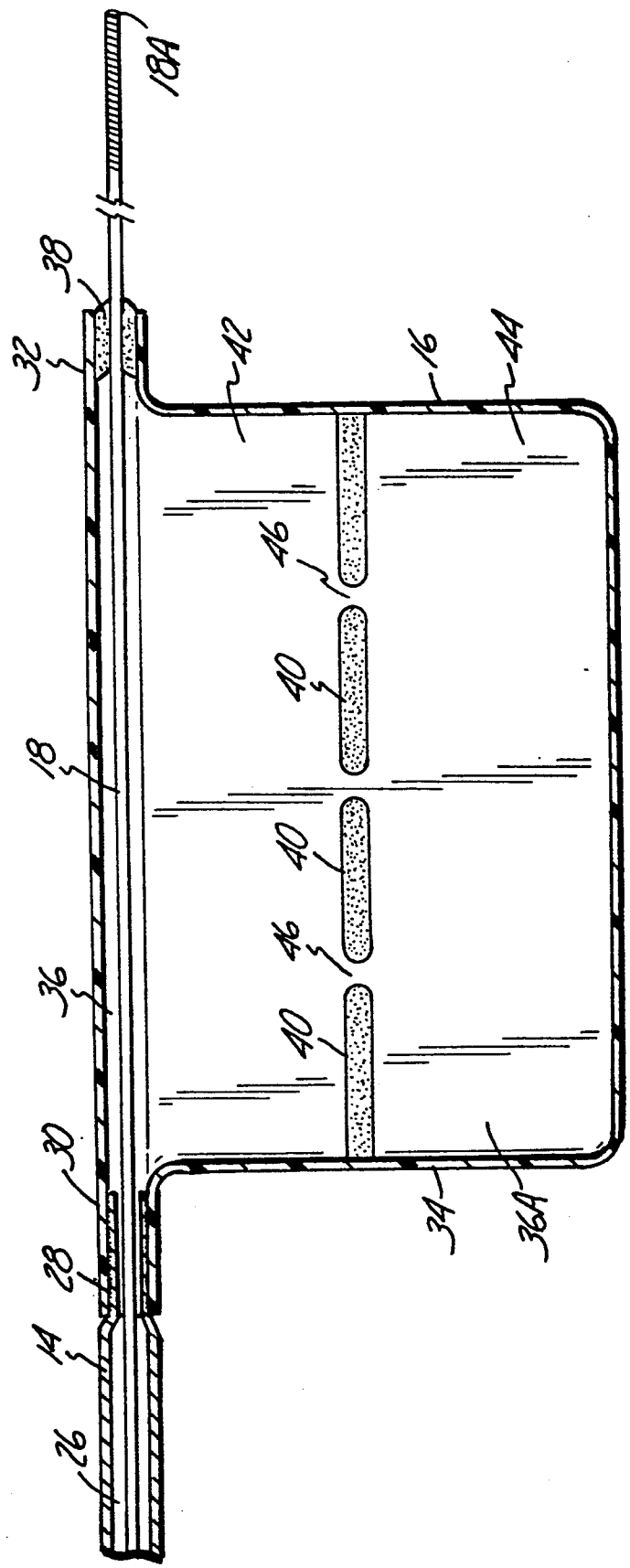
FIG. 2 is a longitudinal sectional view of the balloon of FIG. 1.
Figure 10:
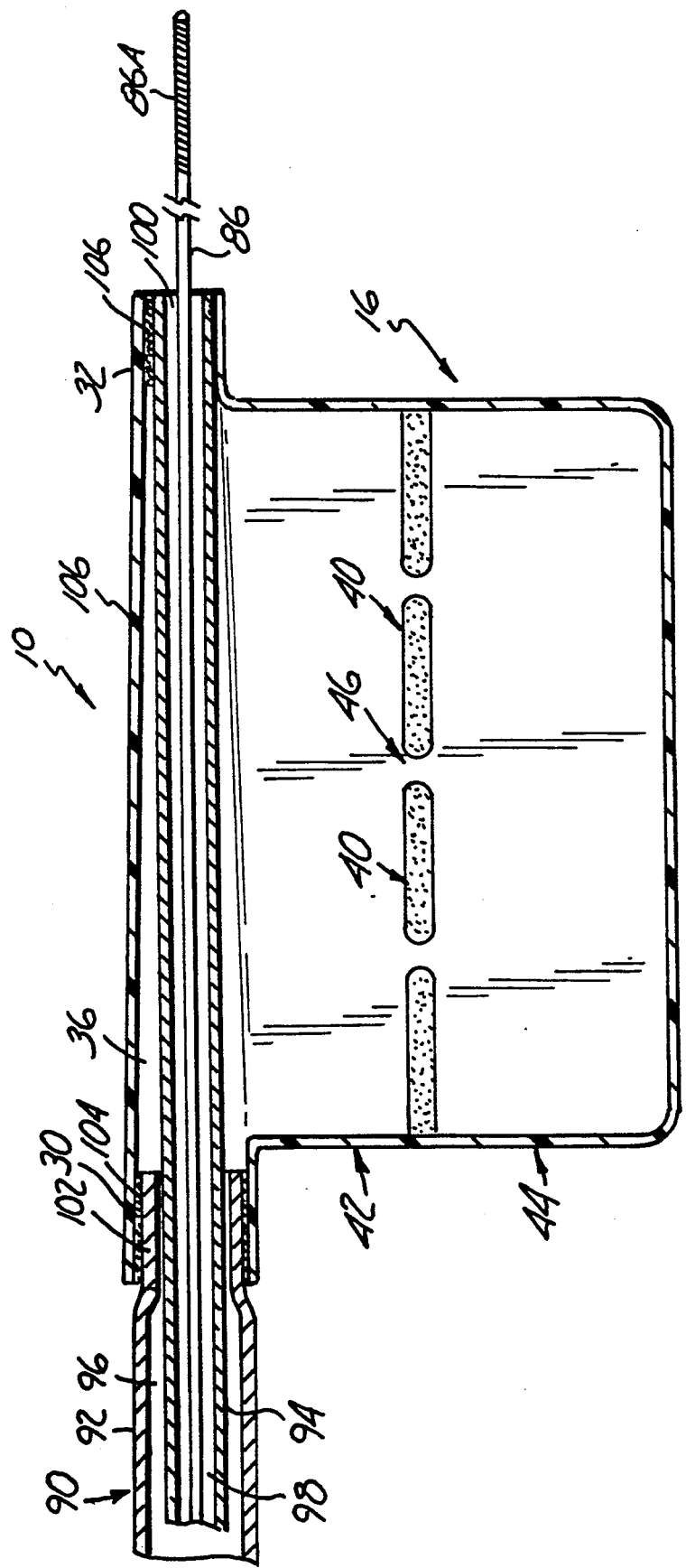
FIG. 10 is a longitudinal sectional view of the balloon of FIG. 9.

FIG. 1 shows a side view of the perfusion balloon catheter 10 for performing dilatation of an artery. Catheter 10 generally includes manifold 12, elongated tubular shaft 14, balloon 16 and fixed wire 18.

Manifold 12 is located at the proximal end of catheter 10 and includes inflation port 20, through which inflation fluid is provided to and withdrawn from balloon 16.

Elongated tubular shaft 14 is a single lumen tube having its proximal end 22 connected to manifold 12 and its distal end 24 connected to balloon 16. Shaft 14 includes lumen 26 (shown in FIG. 2) which extends from proximal end 22 to distal end 24. Lumen 26 of shaft 14 is in fluid communication with inflation port 20 of manifold 12, and also with balloon 16. Shaft 14 is made of any one of a number of different shaft materials typically used for angioplasty catheters, such as polyethylene, polyimide or stainless steel hypotubing. Shaft 14 may be a single material or multiple materials. In some embodiments, shaft 14 includes a distal region which has greater flexibility than its proximal region. As shown in FIG. 2, shaft 14 further includes distal shaft neck 28, which has outer and inner diameters smaller than the outer and inner diameters of shaft 14 for connecting balloon 16.

Fixed wire 18 lies within shaft lumen 26 and balloon 16 and extends out the distal end of balloon 16. Fixed wire 18 terminates with flexible spring tip 18A, which facilitates advancement of catheter 10 through the curves of an artery. Depending upon the particular material used for shaft 14, fixed wire 18 either extends to proximal end 22 of shaft 14, or is connected to shaft 14 at a position located distally of proximal end 22.

As shown in FIGS. 1 and 2, balloon 16 is made of a polymer material such as Surlyn. Balloon 16 includes proximal balloon waist 30, distal balloon waist 32 and balloon body 34. Proximal balloon waist 30 is bonded over neck 26 of shaft 14. Balloon chamber 36 of balloon 16 is in fluid communication with shaft lumen 26. Fixed wire 18 is connected to distal balloon waist 32 by adhesive bond 38 to produce a fluid tight seal at the distal end of balloon 16.

Balloon body 34 is bisected by intermediate longitudinal seal 40 to form first balloon segment 42 and second balloon segment 44. Seal 40 is formed by heat adhesion which bonds opposing intermediate inner surfaces of chamber 36 together. Seal 40 extends from the proximal end of balloon body 34 to the distal end of balloon body 34 with interruptions 46 of seal 40 creating fluid passages between first segment 42 and second segment 44. First segment 42 is further in fluid communication with lumen 26 of shaft 14.

FIG. 3 shows a cross-sectional view of balloon 16 taken along line 3—3 of FIG. 1. Balloon 16, shown in its uninflated state, has outer surface 48 and inner chamber surfaces 36A and 36B, which are connected at seal 40 to form first segment 42 and second segment 44. Fixed wire 18 extends through chamber 36 of first segment 42 and is sealed within distal balloon waste 32 (not shown) by bond 38.

FIG. 4A is an inflated view of balloon 16 of FIG. 3. For purposes of illustration, balloon 16 is shown within artery 50. Under fluid pressure, cavity 36 inflates causing outer surface 48 to incurve and make contact at junction 52 to form first cavity 54 of first segment 42 and second cavity 56 of second segment 44. Expansion of cavities 54 and 56 under fluid pressure causes outer surface 48 to contact and expand artery wall 58 and to press lesion 60 into artery wall 58.

The interaction of outer surface 48 adjacent to junction 52 also forms sinus 62 and sinus 64, which allow passive perfusion of blood through the artery 50 during prolonged inflation of balloon 16. Sinus 62 is located adjacent to seal 40 and is formed by the interaction of outer surface 48 and junction 52 along the length of balloon 16. Sinus 64 is formed by the interaction of outer surface 48, junction 52 and wall 58 of artery 50. Sinus 64 also runs the length of balloon 16. Fixed wire 18 extends through first cavity 54 of first segment 42 and extends out distal balloon waist 32. Bond 38 seals fixed wire 18 within distal balloon waist 32 to form a fluid tight seal at the distal end of balloon 16.

FIG. 4B shows balloon 16 of FIG. 4A with sheath 66 surrounding outer surface 48. Sheath 66 is made of a flexible material which conforms to the general shape of balloon 16 when balloon 16 is inflated. Sheath 66 has an outer surface 68 which contacts wall 58 of artery 50 and presses lesion 60 into wall 58 when balloon 16 is inflated. When sheath 66 is used over balloon 16, sinus 64 is formed by the interaction of outer surface 48, junction 52 and the inner surface of sheath 66. In those embodiments in which it is used, sheath 66 is preferably bonded to the exterior of balloon 16.

FIGS. 5–8B show a second embodiment of the present invention. This second embodiment is similar to the embodiment shown in FIGS. 1–4A, and similar reference characters to those used in FIGS. 1–4A are used to designate similar elements in FIGS. 5–8B. Three essential elements distinguish the second embodiment from the first embodiment. First, guide wire support sleeve 80 is mounted at the distal end of fixed wire 18. The distal end of guide wire support sleeve 80 is generally aligned with the distal end of fixed wire 18. Guide wire support sleeve 80 is bonded by adhesive 82 to fixed wire 18. Guide wire support sleeve 80 includes guide passage 84, which permits transverse movement of guide wire 86 above, external and proximate to catheter shaft 14 and balloon 16.

The location of guide wire 86 external to catheter shaft 14 is the second unique element to the second embodiment. External guide wire 86 permits rapid exchange of catheter 10 over guide wire 86 while guide wire 86 remains in place in the artery with distal spring end 86A of guide wire 86 in position across the stenosis. When balloon 16 is inflated, guide wire 86 occupies a portion of sinus 64.

Finally, seal 40, as shown in FIGS. 5 and 6, has a single, uninterrupted length which is less than the length of balloon 16. Interruptions 46, therefore, are located near the proximal and distal ends of balloon body 34 to provide a fluid passage between first segment 42 and second segment 44.

FIGS. 9–12 show a third embodiment of the perfusion balloon of the present invention disposed at the distal end of a multi-lumen catheter shaft. This embodiment is similar to the previous embodiments shown in FIGS. 1–8A, and therefore similar reference characters to those used in FIGS. 1–8A are used to designate similar elements in FIGS. 9–12. As shown in FIGS. 9–12, balloon 16 is disposed at the distal end of multi-lumen shaft 90. Shaft 90 includes outer tube 92 and inner tube 94. Inner tube 94 extends proximally within outer tube 92, and tubes 92 and 94 are connected at their proximalmost ends to a manifold (not shown) typical of many multi-lumen shaft catheters.

Inflation lumen 96 is defined between the outer wall of inner tube 94 and the inner wall of outer tube 92. Inflation lumen 96 extends from the manifold (not shown) to cavity 36 of balloon 16.

Guide wire lumen 98 extends through the interior of inner tube 94 from the manifold to distal opening 100 at the distal end of catheter 10. Proximal balloon waist 30 is bonded to distal neck 102 of outer shaft 92 by adhesive 104. Distal balloon waist 32 is bonded to a distal end of inner tube 94 by adhesive 106. The outer diameter of distal neck 102 is slightly larger than the outer diameter of the distal end of inner tube 94, which causes a slight proximal-to-distal slant of upper surface 106 of balloon 16.

Guide wire 86 lies within inner tube 94 and extends from the manifold, through lumen 98 and out distal opening 100.

Although the present invention has been described with reference to preferred embodiments, workers skilled in the art will recognize that changes may be made in form and detail without departing from the spirit and scope of the invention.

What is claimed is:

1. A perfusion dilation catheter comprising:
 a shaft having a proximal end, a distal end, and an inflation lumen extending between the proximal and distal end;
 an elongated member extending distally from the distal end of the shaft; and
 a balloon having a proximal end connected to the distal end of the shaft and a distal end connected to the elongated member, the balloon having a first intermediate inner surface connected by a seal to a second intermediate inner surface along a length of the balloon which forms a first inflatable region and a second inflatable region having a proximal and distal end, the first inflatable region being in fluid communication with the inflation lumen, and the second inflatable region being in fluid communication with the first inflatable region; the first and second inflatable regions contacting one another, when inflated, to apply radial outward force and to form a perfusion passage with at least a portion of an outer surface of the first inflatable region contacting at least a portion of an outer surface of the second inflatable region to form the perfusion passage adjacent contacting portions of the first and second inflatable regions, the perfusion passage extending from the proximal end to the distal end of the balloon.

2. The perfusion dilatation catheter of claim 1 wherein the first inflatable region and the second inflatable region are eccentric and are symmetrical relative to the seal.

3. The perfusion dilatation catheter of claim 1 wherein the seal has a length less than a length of the balloon so that a fluid passage which connects the first and second inflatable regions is formed between an end of the balloon and the seal.

4. The perfusion dilatation catheter of claim 1 wherein the seal has a first seal segment and a second seal segment which are not contiguous, and a fluid passage extending between the first and second seal segments which connects the first and second inflatable regions.

5. The perfusion dilatation catheter of claim 1 and further including:
 a flexible sheath which encircles the balloon.

6. The perfusion dilatation catheter of claim 1 and further including:
 a guide wire sleeve carried at a distal end of the elongated member, distal to the balloon.

7. The perfusion dilatation catheter of claim 1 wherein the elongated member is a tube which defines a guide wire lumen.

8. The perfusion catheter of claim 1 wherein the elongated member is a core wire having a spring tip at a distal end.

9. The perfusion catheter of claim 1 wherein the first and second inflatable regions, when inflated, form a pair of generally parallel sinuses which act as the perfusion passage.

10. A dilatation catheter comprising:
 a shaft having a proximal end, a distal end, and an inflation lumen extending from the proximal end to the distal end;
 a balloon having a proximal end attached to the distal end of the shaft and a sealed distal end, the balloon having an outer surface, an inner surface and an interior in fluid communication with the inflation lumen, the balloon having a generally longitudinal seal which connects the inner surface and divides the balloon into a first balloon segment and a second balloon segment, the first balloon segment having its interior in fluid communication with the inflation lumen, and the second balloon segment having its interior connected to the interior of the first balloon segment by a fluid passage, the first and second balloon segments being generally parallel to one another and spaced apart by the seal with the first balloon segment positioned between the shaft and the second balloon segment so that when inflated within an artery the segments push against one another with at least a portion of an outer surface of the first balloon segment contacting at least a portion of an outer surface of the second balloon segment so as to form a perfusion passage adjacent to the contacting portions of the first and second balloon segments which permits blood flow past both the first and second balloon segments.

11. The dilatation catheter of claim 10 and further including:
 an elongated member extending through the interior of the first balloon segment and connected to a distal end of the first balloon segment.

12. The dilation catheter of claim 11 wherein the elongated member is a tube having a guide wire passage extending from its proximal end to its distal end.

13. The dilatation catheter of claim 11 and further including:
 a guide wire sleeve carried at a distal end of the elongated member, distal to the balloon.

14. The dilatation catheter of claim 9 and further including:
 a generally tubular sheath which surrounds the balloon.

15. A perfusion dilatation catheter comprising:
 a shaft having a proximal end, a distal end, and an inflation lumen;
 an elongated member within the shaft and extending distally beyond the distal end of the shaft;
 a first balloon through which the elongated member extends, the first balloon having a proximal end connected to the distal end of the shaft and a distal end connected to the elongated member, the first balloon having an interior in fluid communication with the inflation lumen;
 a second balloon separated from the shaft and the elongated member by the first balloon, the second balloon being connected to the first balloon, having an interior and generally parallel to the first balloon and to the elongated member; and
 means for fluidly connecting the interior of the first balloon to the interior of the second balloon so that when the first and second balloons are inflated they press against one another to apply a radially outward force with at least a portion of an outer surface of the first balloon contacting at least a portion of an outer surface of the second balloon to form a perfusion passage adjacent to the contacting portions.

16. A perfusion dilatation catheter comprising:

a shaft having a proximal end, a distal end, and an inflation lumen extending between the proximal and distal end;

an elongated member comprising a core wire having a spring tip at a distal end, the elongated member extending distally from the distal end of the shaft; and a balloon having a proximal end connected to the distal end of the shaft and a distal end connected to the elongate member, the balloon having a first intermediate inner surface connected by a seal to a second intermediate inner surface, wherein the seal has a length less than a length of the balloon so that a fluid passage which connects a first and a second inflatable region is formed between an end of the balloon and the seal, the first inflatable and the second inflatable region having a proximal end and a distal end, the first inflatable region being in fluid communication with the inflation lumen, wherein the first inflatable region is eccentric relative to the second inflatable region;

the second inflatable region being in fluid communication with the first inflatable region; and the first and second inflatable regions contacting one another, when inflated, to apply radial outward force and to form a perfusion passage adjacent the inflatable regions and extending from the first proximal end to the distal end of the balloon.

17. A perfusion dilatation catheter comprising:

a shaft having a proximal end, a distal end, and an inflation lumen extending between the proximal and distal end;

an elongated member extending distally from the distal end of the shaft; and a balloon having a proximal end connected to the distal end of the shaft and a distal end connected to the elongated member, the balloon having a first intermediate inner surface connected by a seal to a second intermediate inner surface along a length of the balloon wherein the seal has a length less than a length of the balloon so that a fluid passage which connects a first and second inflatable region is formed between an end of the balloon and the seal, thereby forming a first inflatable region and a second inflatable region having a proximal end and a distal end, the first inflatable region being in fluid communication with the inflation lumen, and the second inflatable region being in fluid communication with the first inflatable region, wherein the first inflatable region is eccentric relative to the second inflatable region, and wherein the first and second inflatable regions, when inflated, form a pair of generally parallel sinuses adjacent the inflatable regions which act as the perfusion passage.

* * * * *

UNITED STATES PATENT AND TRADEMARK OFFICE
CERTIFICATE OF CORRECTION

PATENT NO. : 5,232,446
DATED : August 3, 1993
INVENTOR(S) : MICHELLE ARNEY

It is certified that error appears in the above-identified patent and that said Letters Patent is hereby corrected as shown below:

Col. 6, line 34, delete "dilation", insert --dilatation--

Col. 7, line 13, delete "elongate", insert --elongated--

Signed and Sealed this

Fifth Day of April, 1994

Attest:

BRUCE LEHMAN

Attesting Officer

Commissioner of Patents and Trademarks